United States Patent [19]
Insall

[11] Patent Number: 5,571,197
[45] Date of Patent: *Nov. 5, 1996

[54] KNEE POSITION INDICATOR

[76] Inventor: John N. Insall, 227 Griffin Ave., Scarsdale, N.Y. 10583

[*] Notice: The term of this patent shall not extend beyond the expiration date of Pat. No. 5,443,518.

[21] Appl. No.: 443,412

[22] Filed: May 17, 1995

Related U.S. Application Data

[63] Continuation of Ser. No. 94,636, Jul. 20, 1993, Pat. No. 5,443,518.

[51] Int. Cl.⁶ ............................................. A61F 2/38
[52] U.S. Cl. ................................................ 623/20
[58] Field of Search ................................... 623/20

[56] References Cited

U.S. PATENT DOCUMENTS

| | | | |
|---|---|---|---|
| 3,837,009 | 9/1974 | Walker | 3/1 |
| 4,213,209 | 7/1980 | Insall et al. | 3/1.911 |
| 4,216,549 | 8/1980 | Hillberry et al. | 3/1.911 |
| 4,634,444 | 1/1987 | Noiles | 623/20 |
| 4,714,473 | 12/1987 | Bloebaum | 623/20 |
| 5,326,363 | 7/1994 | Aikins | 623/20 |
| 5,443,518 | 8/1995 | Insall | 623/20 |

OTHER PUBLICATIONS

Tekscan, Inc. —Product Description —Copyright 1989.

Primary Examiner—Randy C. Shay
Attorney, Agent, or Firm—Cary R. Reeves

[57] ABSTRACT

A tibial knee component includes reference marks to which a surgeon can reference the location of the point of contact between the tibial component and a femoral knee component. In one embodiment of the invention, the femoral component also includes reference marks to aid the surgeon in determining the contact point and to aid in orienting the knee in specific predetermined degrees of flexion.

7 Claims, 2 Drawing Sheets

KNEE POSITION INDICATOR

This is a continuation of application Ser. No. 08/094,636 filed Jul. 20, 1993, now U.S. Pat. No. 5,443,518.

BACKGROUND OF THE INVENTION

The present invention relates to artificial knee joint components containing index marks to indicate the position of one component with respect to the other.

During knee joint replacement surgery it is desirable to know where the contact point between the femoral and tibial components lies relative to the anterior-posterior dimension of the tibia. This information can aid in aligning the components for proper location of the initial contact between the femoral and tibial components. It is also informative to know how the location of this contact point changes during flexion and extension of the knee joint. If the contact point shifts posteriorly several millimeters, known as rollback, and the posterior cruciate ligament (PCL) is intact, the PCL is causing at least some of the rollback and therefore is functional. A surgeon can then make informed decisions as to the appropriate type of implant, the balancing of soft tissue tension around the knee joint by carefully severing certain tissues, and the adjustment of component alignment. With prior knee joint components, both the implants themselves and the provisional implants used for size selection, there is no indicator to aid in quantifying contact point location or contact point change in location.

SUMMARY OF THE INVENTION

This invention provides a means for visualizing the contact point location and gauging its change in location with knee flexion and extension. The tibial component includes reference marks with which the surgeon can compare contact point location. In one embodiment of the invention, the femoral component also includes reference marks to aid the surgeon in determining the contact point and to aid in orienting the knee in specific predetermined degrees of flexion.

DETAILED DESCRIPTION OF THE INVENTION

Figure 1:
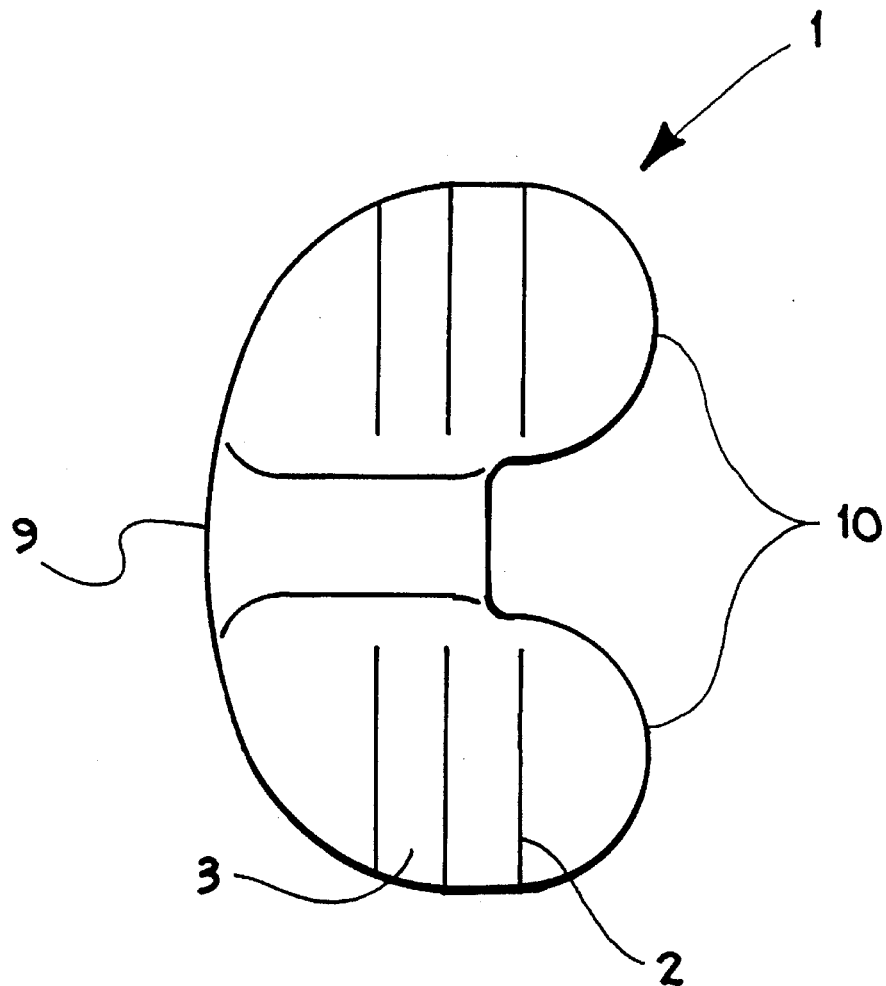
FIG. 1 is a plan view of the tibial knee component of this invention.
Figure 2:
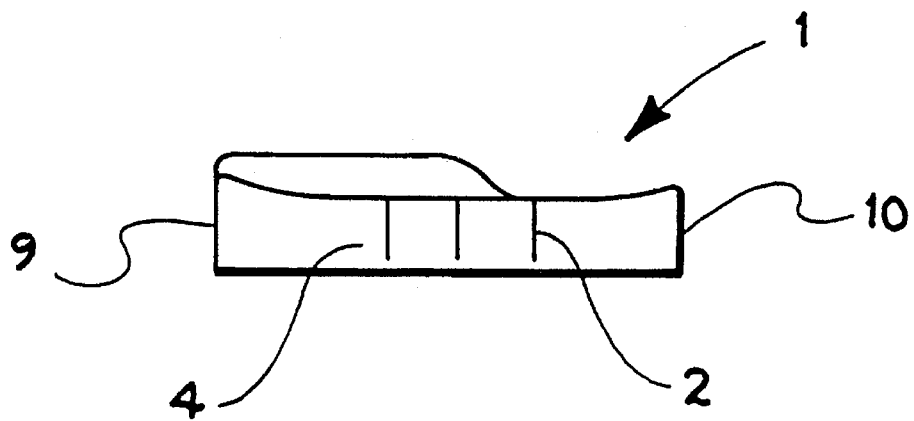
FIG. 2 is a side view of the component of FIG. 1.

Referring to FIGS. 1–2, a tibial component 1 of an artificial knee joint has a superior surface 3, an anterior surface 9, a posterior surface 10 and medial and lateral surfaces or sides, one 4 of which is indicated. The tibial component 1 includes reference marks 2 which preferably extend across at least part of the superior surface 3 and down at least one of the sides 4 of the tibial component. It has been found that three marks 6 spaced approximately 5 mm apart and located midway between the anterior and posterior surfaces of the tibial component work well. These marks are preferably located on both sides of the tibial component as shown. Such marks are made by any appropriate method such as by engraving or where the parts are molded by incorporating the marks into the mold.

Figure 3:
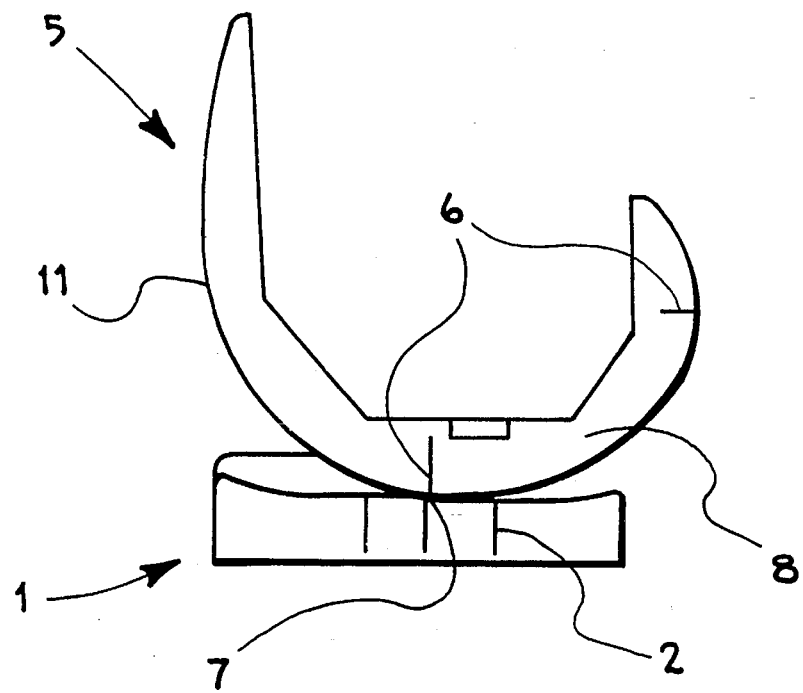
FIG. 3 is a side view of the tibial knee component of FIG. 1 and a femoral knee component with the components positioned as they would be at full extension in vivo.
Figure 4:
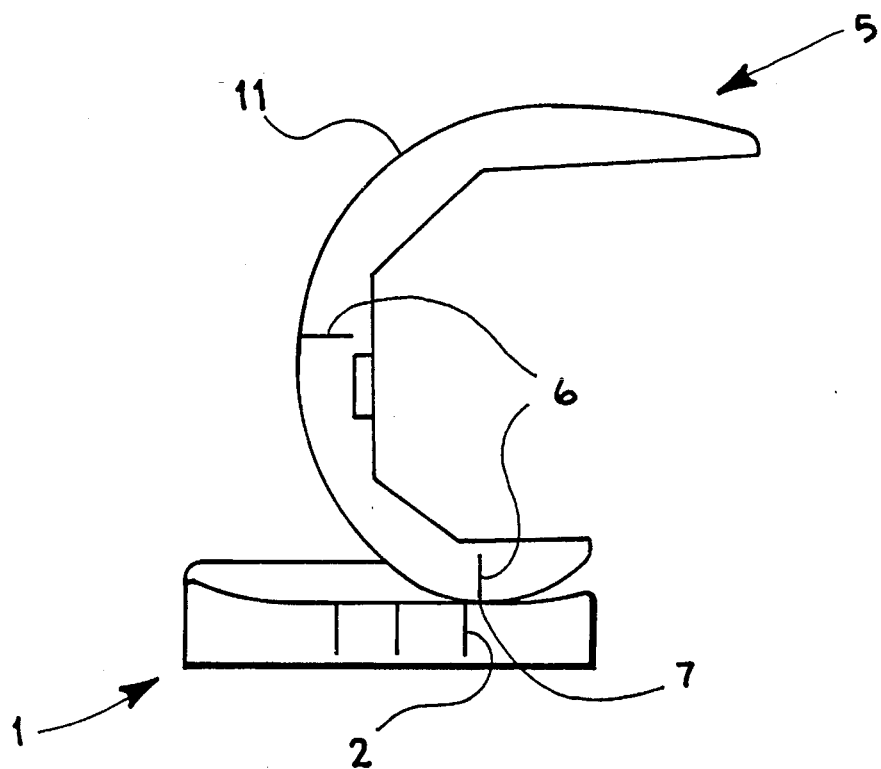
FIG. 4 is side view of the components of FIG. 3 with the components positioned as they would be at 90 degrees of knee flexion in vivo.

FIGS. 3–4 depict a femoral component 5 having medial and lateral surfaces or sides, one 8 of which is indicated. The femoral component 5 includes reference marks 6 corresponding to selected flexion angles of the knee, for example zero degrees of flexion and 90 degrees of flexion as shown. These marks 6 are located radially with respect to the outer curvature, or articular surface 11, of the femoral component so as to approximate the contact point 7 between the femoral component 5 and the tibial component 1 at the selected flexion angles. These marks 6 are also made by an appropriate method such as by engraving.

In use, the surgeon would note the position of the contact point 7 with respect to the tibial component 1 at a predetermined angle of flexion by comparing the contact point 7 position to the reference marks 2 on the tibial component 1. This relative position gives the surgeon an indication of correct component alignment. In the preferred embodiment shown, the femoral component 5 contains reference marks 6 to aid in determining the contact point 7 at selected flexion angles, for example zero and ninety degrees of flexion. However, the contact point 7 may be determined without these marks 6 or at flexion angles between these marks by approximating its location visually and then referring to the tibial reference marks 2 to locate its relative position on the tibial component 1.

To determine rollback, the relative position of the contact point 7 on the tibia is compared at two different flexion angles. For example, in FIG. 3, the components are shown oriented at zero degrees of flexion. The surgeon would note the relative position of the components using the reference marks as described above and then reposition the knee to another flexion angle such as 90 degrees as shown in FIG. 4. The surgeon would again note the relative position of the components and compare this position to the prior one. The difference in the positions is the amount of rollback.

The preferred embodiment of the invention contains reference marks on both the medial and lateral sides of the tibial component so that the surgeon can determine component position from either side of the knee. Having marks on both sides also allows the surgeon to compare medial and lateral rollback which yields further information regarding joint function. Also, the invention described in this disclosure can be incorporated in actual implant components as well as provisional or trial components used for selecting the actual implant components to be used.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. An apparatus for determining knee position during knee joint replacement comprising a femoral component and a tibial component the tibial component having medial, lateral and superior tibial surfaces, the superior tibial surface configured to accommodate articulation with the femoral component, at least one of the medial and lateral tibial surfaces including an elongated, linear, tibial reference mark extending down the at least one surface for visually indicating relative location between the tibial component and the femoral component, the tibial reference mark being visible when the tibial component and the femoral component are implanted so that in use the relative location of a contact point between the tibial component and the femoral component is visually indicated by the contact point's location relative to the reference mark, the contact point's location relative to the reference mark changing as the components are articulated relative to one another.

2. The apparatus of claim 1 wherein the tibial component further comprises anterior and posterior surfaces and wherein the tibial reference mark is located approximately midway between the anterior and posterior surfaces.

3. The apparatus of claim 1 wherein the femoral component has medial, lateral and articular femoral surfaces and at least one of the medial and lateral femoral surfaces has first and second elongated, linear, femoral reference marks corresponding to first and second degrees of flexion the marks extending down the surface and being located radially with respect to the articular surface so as to indicate the contact point between the femoral component and the tibial component at the first and second degrees of flexion respectively, the femoral reference marks being visible when the femoral component and the tibial component are implanted.

4. The apparatus of claim 1 wherein the reference mark further extends across a portion of the superior tibial surface.

5. The apparatus of claim 1 wherein the reference mark is in the form of a depression formed into one of the medial and lateral surfaces.

6. An apparatus for determining knee position during knee joint replacement comprising:

a prosthetic tibial knee component having medial, lateral and superior tibial surfaces; and a femoral knee component, the superior tibial surface configured to accommodate articulation with the femoral knee component, wherein at least one of the medial and lateral tibial surfaces contains at least three uniformly spaced tibial reference marks extending down the at least one surface for visually indicating relative location between the tibial knee component and the femoral knee component.

7. An apparatus for determining knee position during knee joint replacement comprising a femoral component and a tibial component, the tibial component having medial, lateral and superior tibial surfaces, the superior tibial surface configured to accommodate articulation with the femoral component, the medial and lateral surfaces intersecting the superior tibial surface, at least one of the medial and lateral tibial surfaces including a tibial reference mark extending at least part way down the at least one surface beginning from the intersection of the at least one surface with the superior tibial surface for visually indicating the relative location of a contact point on the superior tibial surface between the tibial component and the femoral component when the components are viewed from the side, the tibial reference mark being visible when the tibial component and the femoral component are implanted so that in use the relative location of the contact point between the tibial component and the femoral component is visually indicated by the contact point's location relative to the reference mark, the location of the contact point relative to the reference mark changing as the components are articulated with respect to one another.

* * * * *